(12) United States Patent
Hassett

(10) Patent No.: US 11,660,119 B2
(45) Date of Patent: May 30, 2023

(54) CATHETER SYSTEM FOR LEFT HEART ACCESS

(71) Applicant: Medtronic, Inc., Minneapolis, MN (US)

(72) Inventor: Jim Hassett, Eden Prairie, MN (US)

(73) Assignee: Medtronic, Inc., Minneapolis, MN (US)

( * ) Notice: Subject to any disclaimer, the term of this patent is extended or adjusted under 35 U.S.C. 154(b) by 866 days.

(21) Appl. No.: 16/408,759

(22) Filed: May 10, 2019

(65) Prior Publication Data

US 2019/0262037 A1 Aug. 29, 2019

Related U.S. Application Data

(63) Continuation of application No. 14/715,788, filed on May 19, 2015, now abandoned.

(51) Int. Cl.
| | | |
|---|---|---|
| *A61B 18/14* | (2006.01) | |
| *A61B 18/00* | (2006.01) | |
| *A61B 5/00* | (2006.01) | |
| *A61B 5/296* | (2021.01) | |
| *A61B 17/00* | (2006.01) | |
| *A61B 17/34* | (2006.01) | |

(52) U.S. Cl.
CPC .......... *A61B 17/3478* (2013.01); *A61B 5/296* (2021.01); *A61B 5/6852* (2013.01); *A61B 18/1477* (2013.01); *A61B 2017/00247* (2013.01); *A61B 2017/00327* (2013.01); *A61B 2017/00455* (2013.01); *A61B 2018/0038* (2013.01)

(58) Field of Classification Search
CPC ................ A61B 5/6852; A61B 5/0492; A61B 2018/0293; A61B 2018/1425; A61B 17/3478; A61B 2017/00455; A61B 2017/00327; A61B 2017/00247
See application file for complete search history.

(56) References Cited

U.S. PATENT DOCUMENTS

| | | | |
|---|---|---|---|
| 3,995,623 A | 12/1976 | Blake et al. | |
| 4,329,993 A | 5/1982 | Lieber et al. | |
| (Continued) | | | |

FOREIGN PATENT DOCUMENTS

| | | |
|---|---|---|
| EP | 2018208 | 9/2012 |

OTHER PUBLICATIONS

European Office Action dated Sep. 18, 2020 issued in corresponding European Application No. 16793512.1.

(Continued)

*Primary Examiner* — Eun Hwa Kim
(74) *Attorney, Agent, or Firm* — Michael Best & Friedrich, LLP

(57) ABSTRACT

A pair of cooperating catheters are used together to provide rapid access to the Left heart for diagnostic or therapeutic interventions. The initial entry point for the catheter pair is the groin. The pair of catheters can be used to carry out an electrographic determination of the location of the Fossa Ovalis on the septum. Features on the Catheter system permit quick and reliable confirmation of the catheter location via echo or x-rays. Once across the septum the inner catheter is removed from the outer catheter and a standard intervention may be carried out through the lumen of the outer catheter.

11 Claims, 15 Drawing Sheets

(56) References Cited

U.S. PATENT DOCUMENTS

| | | | |
|---|---|---|---|
| 5,254,088 A | 10/1993 | Lundquist et al. | |
| 5,364,351 A * | 11/1994 | Heinzelman | A61M 25/0147 604/95.04 |
| 5,389,100 A | 2/1995 | Bacich et al. | |
| 5,391,172 A | 2/1995 | Williams et al. | |
| 5,601,601 A | 2/1997 | Tal et al. | |
| 6,554,794 B1 | 4/2003 | Mueller et al. | |
| 7,083,588 B1 | 8/2006 | Shmulewitz et al. | |
| 7,270,662 B2 | 9/2007 | Visram et al. | |
| 7,691,095 B2 | 4/2010 | Bednarek et al. | |
| 8,114,110 B2 | 2/2012 | Bednarek et al. | |
| 9,095,683 B2 | 8/2015 | Hall et al. | |
| 9,358,039 B2 | 6/2016 | Kimmel et al. | |
| 9,597,146 B2 | 3/2017 | Davies et al. | |
| 9,775,643 B2 | 10/2017 | Leeflang et al. | |
| 9,848,943 B2 | 12/2017 | Beeckler et al. | |
| 10,166,070 B2 | 1/2019 | Davies et al. | |
| 10,219,857 B2 | 3/2019 | Sherman et al. | |
| 10,232,146 B2 | 3/2019 | Braithwaite et al. | |
| 2004/0044350 A1 | 3/2004 | Martin et al. | |
| 2005/0159738 A1* | 7/2005 | Visram | A61B 18/1492 606/41 |
| 2006/0015085 A1* | 1/2006 | Bates | A61B 17/3478 604/508 |
| 2006/0074398 A1 | 4/2006 | Whiting et al. | |
| 2007/0021648 A1 | 1/2007 | Lenker et al. | |
| 2007/0083168 A1* | 4/2007 | Whiting | A61M 25/007 604/264 |
| 2007/0270751 A1 | 11/2007 | Stangenes et al. | |
| 2009/0299202 A1* | 12/2009 | Krishnan | A61B 5/0036 606/191 |
| 2012/0109079 A1 | 5/2012 | Asleson et al. | |
| 2013/0274784 A1 | 10/2013 | Lenker et al. | |
| 2013/0304051 A1 | 11/2013 | Kimmel et al. | |
| 2014/0088497 A1 | 3/2014 | Campbell et al. | |
| 2015/0258270 A1* | 9/2015 | Kunis | A61M 25/0074 604/506 |

OTHER PUBLICATIONS

Oct. 22, 2018 USPTO Office Action (U.S. Appl. No. 14/715,788)—Our Matter 5266.
Dec. 15, 2017 USPTO Office Action (U.S. Appl. No. 14/715,788)—Our Matter 5266.
Dec. 18, 2018 USPTO Office Action (U.S. Appl. No. 14/715,788)—Our Matter 5266.
Dec. 28, 2016 PCT Search Report (Serial No. PCT/US16/32053)—Our Matter 5448.
Mar. 30, 2018 USPTO Office Action (U.S. Appl. No. 15/075,317)—Our Matter 5327.
Aug. 25, 2017 USPTO Office Action (U.S. Appl. No. 14/715,788)—Our Matter 5266.
Sep. 8, 2017 USPTO Office Action (U.S. Appl. No. 15/075,317)—Our Matter 5327.
European Search Report dated Feb. 19, 2019.

* cited by examiner

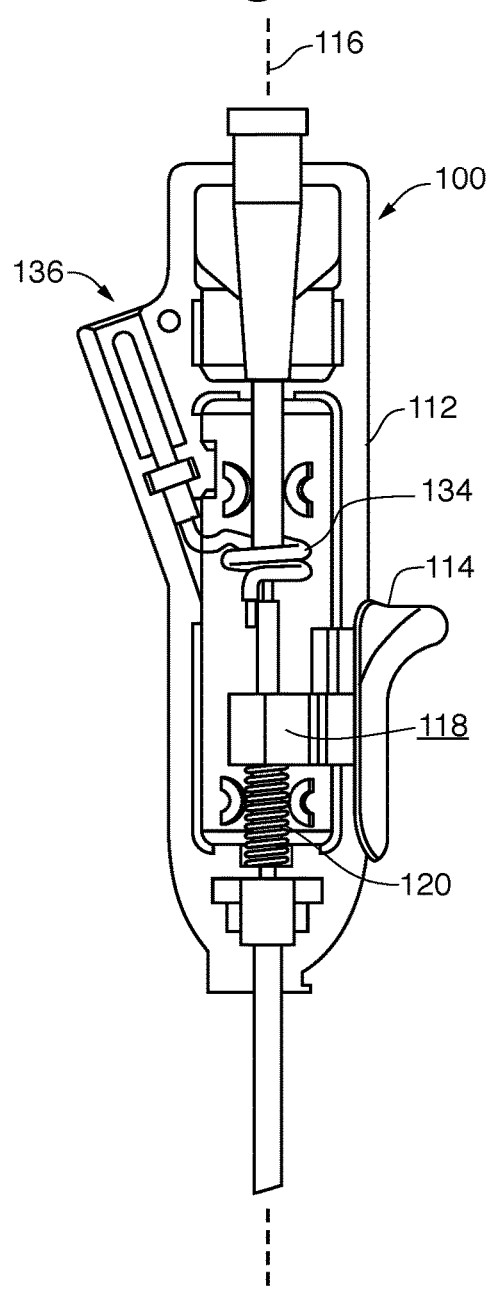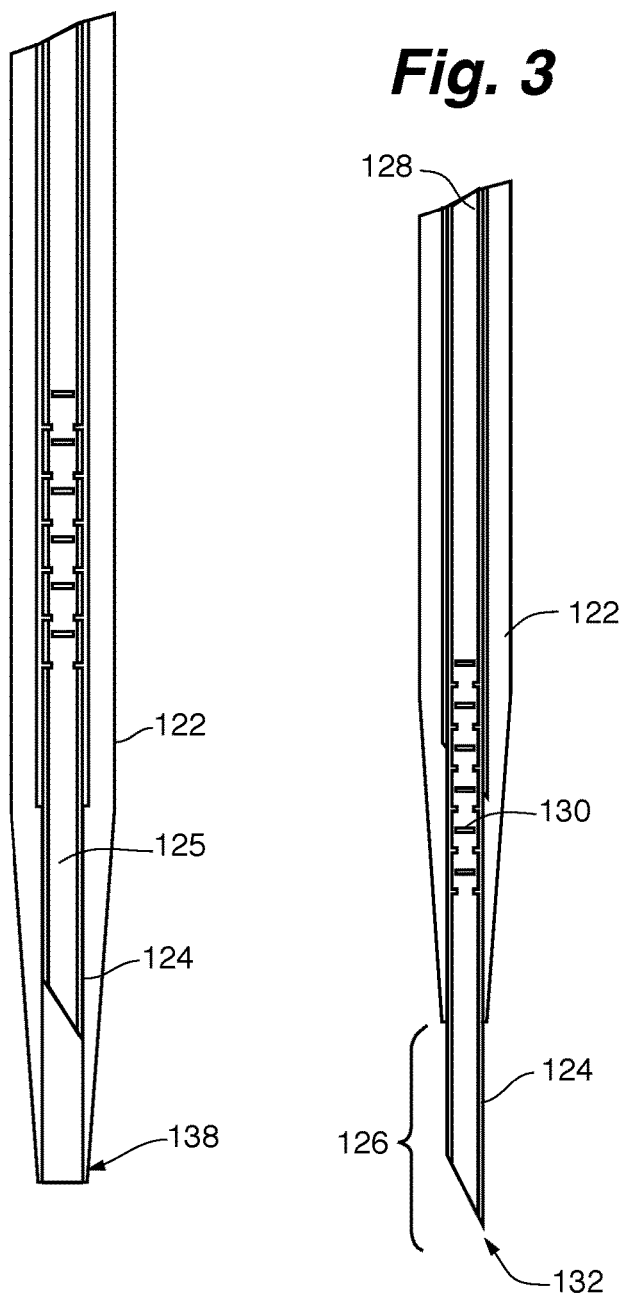

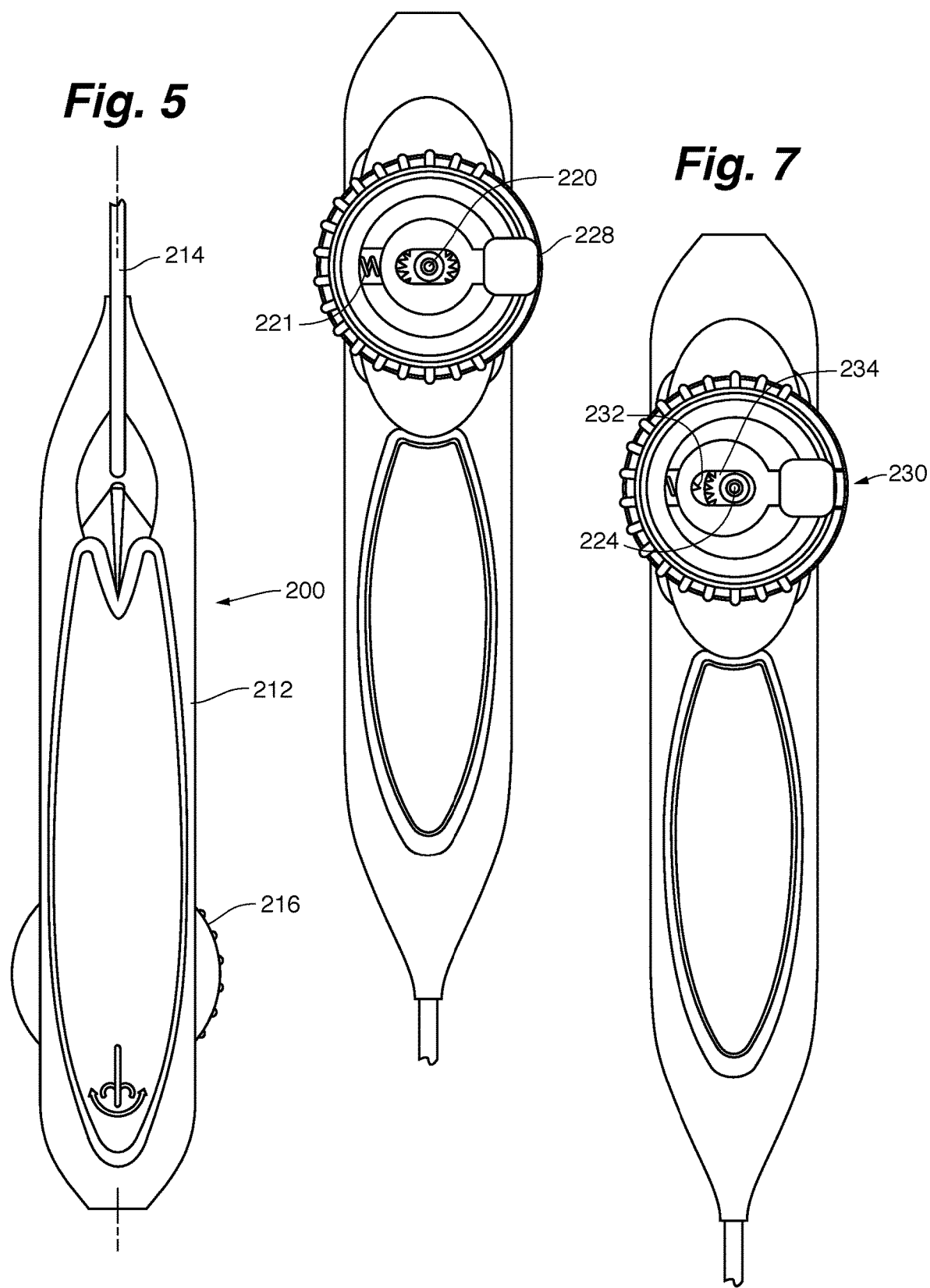

CATHETER SYSTEM FOR LEFT HEART ACCESS

BACKGROUND OF THE INVENTION

Many patients undergo diagnostic or interventional procedures in their left heart. For example a patient with atrial fibrillation may undergo an electrophysiological study inside the chambers of the left heart to determine the physical location of the source of the arrhythmia. This may require the use of electrophysiology (EP) catheters positioned in side the left heart and in contact with the walls of the heart to make electrical measurements to determine the location and propagation properties of the arrhythmia. In some instances a particular location may be an anatomic defect that can be ablated by yet another catheter system. In a similar fashion a patient may undergo left heart catheterization to receive a Left Atrial Appendage (LAA) Occlusion device that is placed in the LAA.

Although these procedures are becoming routine there is a need to improve the devices that allow the physician to gain access to the left heart from the right side of the heart and the venous system. The present standard of care involves the use of a stiff straight catheter to reach the right atrium (RA) from an entry site in the leg near the groin. Typically the venous system is accessed in the groin via the familiar Seldinger procedure. With the conventional catheter placed in the RA a supplemental and exposed needle is advanced out of the conventional catheter and it is used to approach and pierce the septal wall dividing the right heart from the left heart.

This technique is cumbersome, requires a substantial amount of fluoroscopic exposure to both the patent and the physician and is potentially dangerous of several reasons.

At the conclusion of the intervention the conventional catheters are removed and the wound in the groin is treated.

SUMMARY OF THE INVENTION

There are two outer catheters and one inner catheter described and claimed. The inner catheter may be used with either of the two outer catheters and these two combined or paired embodiments are shown and claimed.

The inner catheter can be used with conventional catheters as well but is less effective and more cumbersome to use in that configuration.

The paired catheters are useful for carrying out a method of finding and crossing the fossa ovalis and the method is described and claimed.

The two pairs of interacting devices are referred to in the specification as "Guider with Lancer" in a first embodiment and "Flexor with Lancer" in a second embodiment.

In either case the two devices are coupled together and used together to interact together to carry out steps in an electrographic location procedure or method. The inner catheter Lancer device is supported by its companion outer catheter and together they are used to electrically probe the septal wall surface to determine electrographically the location of the fossa ovalis (FO). The Lancer includes an echogenic piercing tip that may be deployed to extends from the distal tip for piecing the FO. The distal tip is sufficiently opaque to x-rays to be seen radiographically and reflective enough to be visualized using ultrasound.

With the specific FO location identified electrographically and verified with another and different modality the Lancer device may be used cross the septum with a deployable needle. Once across the septum the Guider or Flexor may be advanced into the left heart and used to approach the walls of the left atrium. When a desirable location is reached the Lancer is uncoupled from the Guider or Flexor and Lancer is withdrawn from Guider or Flexor.

Therefore in use the Guider device or Flexor device supports and places the encased Lancer device at the wall of the septum. By dragging the pair down the septal wall the FO is found with an electrographic electrode that collects EMG signal at the septum to locate the ideal location for crossing into the left heart. It is important to note that this procedure is carried out with the electrically conductive needle retracted.

With the desired treatment location found the Lancer device remains stationary and the septum is punctured with the same device. Although complex electrically and electrographically it is quicker than the conventional blind probing that is the current state of the art.

The common law trademarks Lancer, Flexor and Guider have been adopted to identify the electrographic, dilating crossing catheter Lancer, and the guiding catheters Flexor and Guider. The marks are owned by Rhythm Xience of Minneapolis, Minn.

BRIEF DESCRIPTION OF THE DRAWINGS

FIG. 1 is a cross-section of inner catheter Lancer;

FIG. 2 is a cross section of the distal tip of Lancer with the puncture element withdrawn;

FIG. 3 is a cross section of the distal tip of Lancer with the puncture element deployed;

FIG. 5 is a top view of the outer catheter Flexor;

FIG. 6 is bottom view of the outer catheter Flexor;

FIG. 7 is a bottom view of the outer catheter Flexor;

FIG. 10 B is a schematic view of the Flexor distal tip;

FIG. 10 C is a schematic view of the Flexor distal tip;

DETAILED DESCRIPTION OF THE INVENTION

Figure 4:
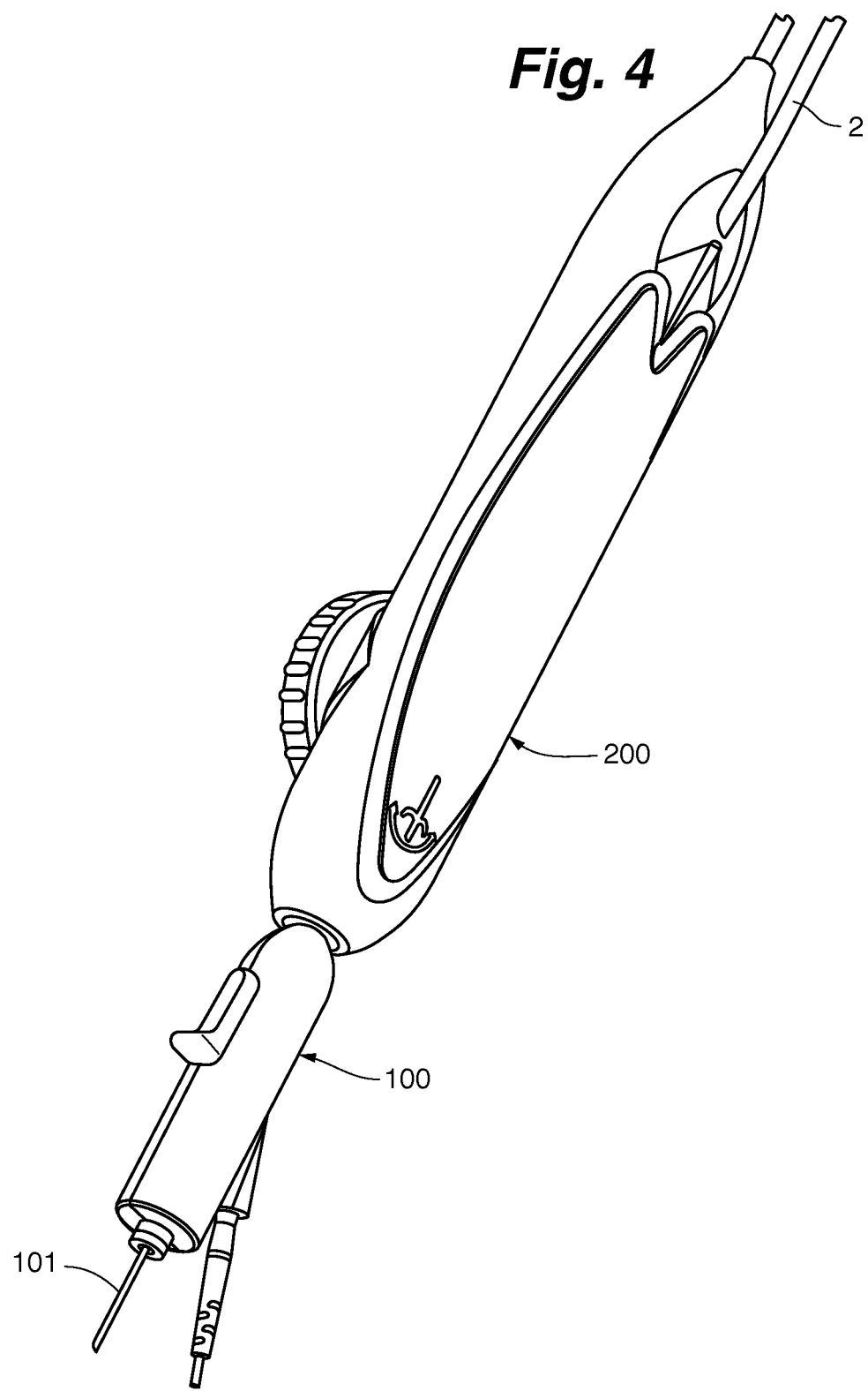
FIG. 4 is a perspective view of the inner catheter Lancer coupled to exterior catheter Flexor.

The overall context of the invention will be described.
The structural features of Guider will be described.
The structural features of Flexor will be described.
The structural features of Lancer will be described.
The method of using Lancer with a companion device will be described.

Lancer Device

The Lancer device is a device to perforate the septum of the heart and dilate that puncture. It is carried in the handle and adapted for sliding motion. It also has electrode connections and functions as a probing electrode. The Lancer device has an internal lumen that can support and carry a guide wire. This permits Lancer to follow over a guide wire.

Turning to FIG. 1 Lancer generally designated 100. There is user interface handle 112. A thumb operated slide 114 is carried in the handle 112 and adapted for sliding motion along the axis 116 of Lancer. In operation the thumb slide 114 forces a tang 118 to compress a spring 120 located along and concentric with the axis 116. Motion of the thumb slide 114 toward the distal end of the lancer causes the electrode/needle distal assembly 125 (FIG. 2) to emerge as identified at 126 (FIG. 3) from the casing 122, as seen in FIG. 2 and FIG. 3 respectively.

The distal assembly has three important features. The hypo-tube 128, such as is shown in FIG. 3, has series of laser-machined partially circumferential slits typified by slit 130 which cooperate together to render the distal tip assembly flexible in any direction or plane and be compliant with the shape of a companion catheter. The distal tip is cut to form a piercing tip 132. This tip is electrically coupled via wire 134 to the connector generally designated 136. The distal sheath casing 122 tapers to a small diameter seen near ref numeral 138, This tapered shape serves as a dilation surface 138.

FIG. 4 shows the Lancer 100 coupled to the companion Flexor 200 device. In general the Lancer is carried within Flexor and they are moved together as a single unit. The Lancer is supported by Flexor and in general the Lancer stiffens the Flexor and functions in part as a stylet to help the operation of Flexor 200.

Flexor Device

FIG. 5 is a top view of the outer catheter Flexor 200 showing the appearance of the top of the handle 212. The Flexor sheath 214 extends form the distal end of handle 212 while the control knob 216 is located near the proximal end of the handle. The control knob turns on a control axis 220 defined by axel 224 orthogonal to the Flexor axis 218.

In use the physician turns the control knob with his left hand and uses the thumb of the left hand to activate the control button 228. When this button is depressed as depicted at ref numeral 230 the tooth 232 disengages from lock pinion gear 234. In the depressed or activated state the motion of the knob is unlocked and the control knob may be turned to steer or flex the distal tip of the device. When released the tooth 232 urged by spring pressure of compression spring 221.

Figure 8:
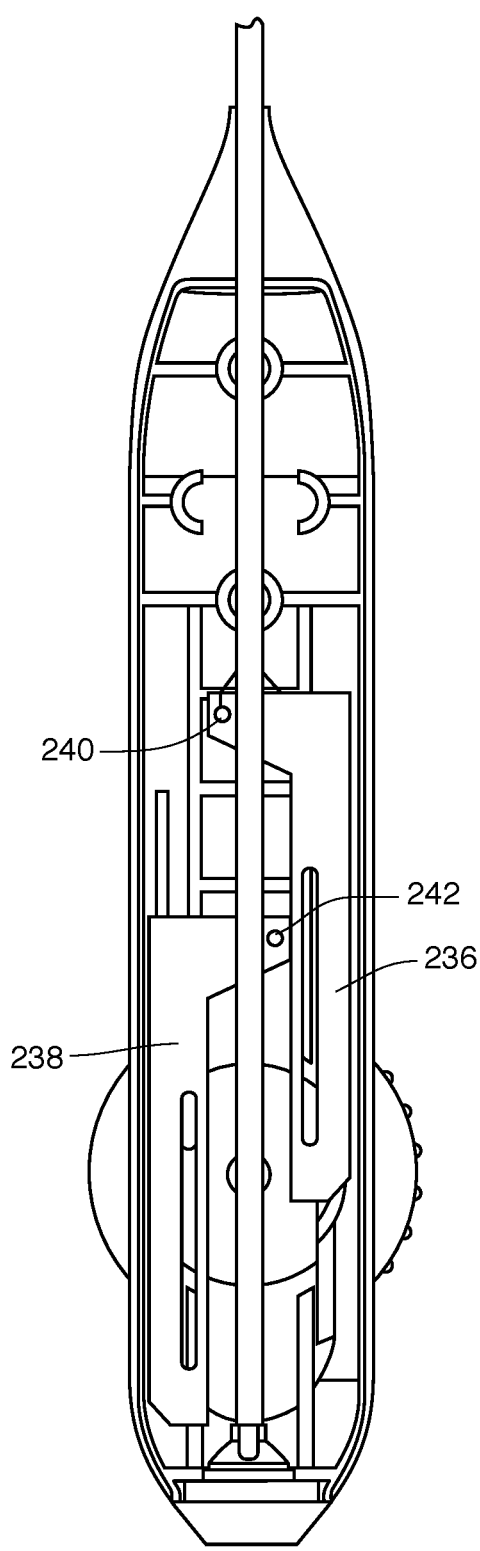
FIG. 8 is a cutaway view of the interior of Flexor.
Figure 9:
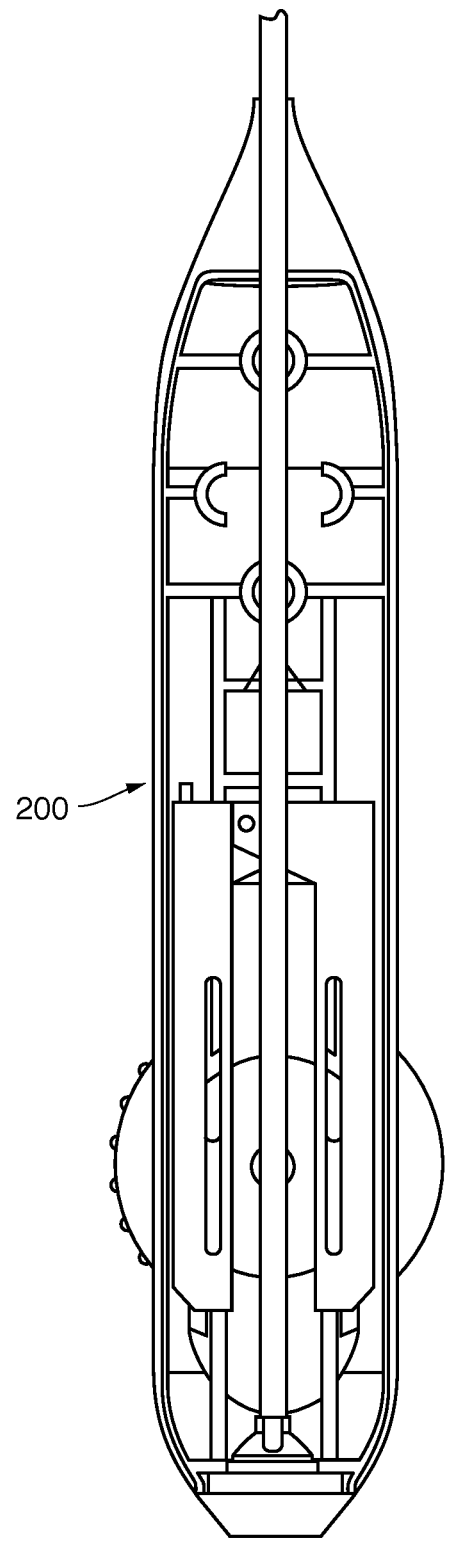
FIG. 9 is a cutaway view of the interior of Flexor.

FIG. 8 and FIG. 9 show a cutaway of the interior of the Flexor 200. The pinion 234 engages both rack 236 and rack 238. Rotation of the pinion 234 drives the racks, with each rack driven in the opposite direction. Cable anchors 242 and cable anchor 240 are moved with respect to each other providing traction to the pulls wires (not seen) that deflect the deflectable distal tip 244 through an arc in a plane.

Figure 10A:
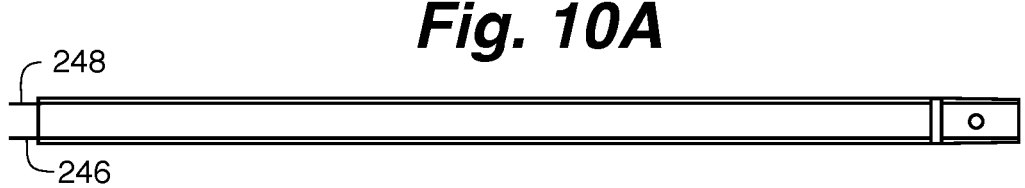
FIG. 10 A is a schematic view of the Flexor distal tip.
Figure 10B:
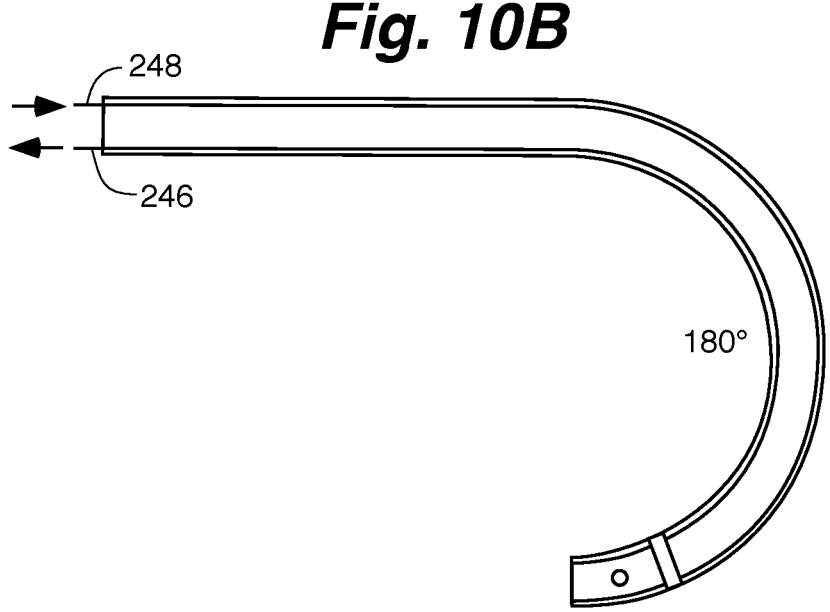
Figure 10C:
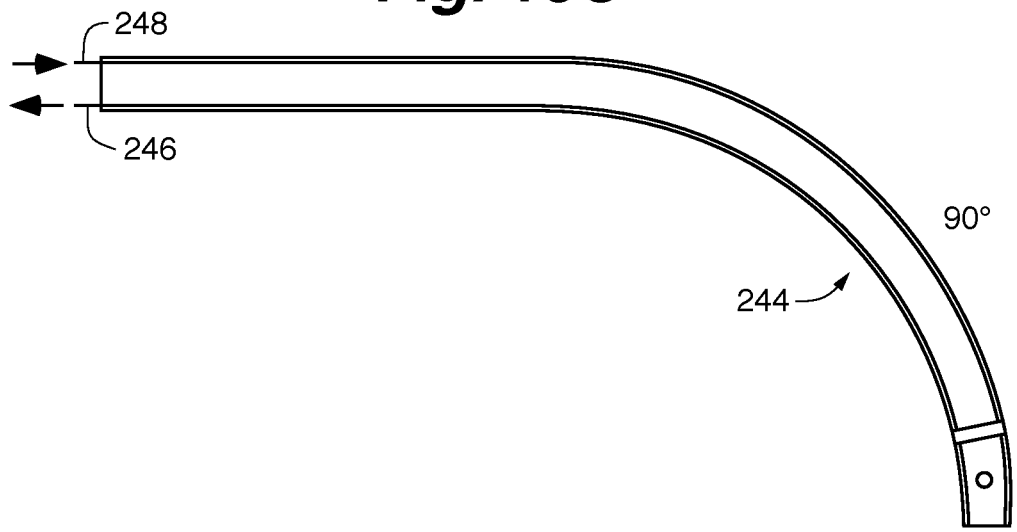

FIG. 10A shows the deflectable distal tip 244 in its un-deflected state corresponding to the rack positions seen in FIG. 9. FIG. 10 B shows the deflectable tip moving through a 180 arc driven by pull wire 246 and pull wire 248, each connected to its respective cable anchor 240 or 242. This curvature corresponds to the rack positions seen in FIG. 8. FIG. 10c shows an intermediate position corresponding to a deflection of approximately 90 degrees.

Figure 11:
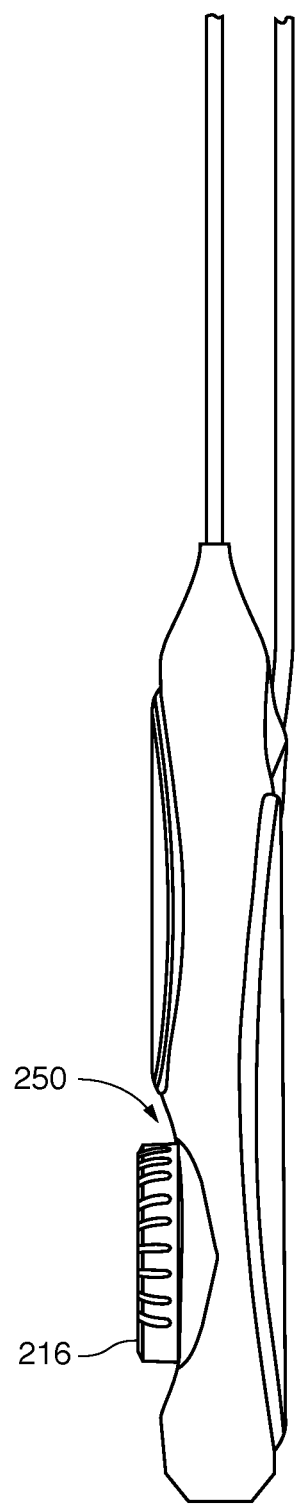
FIG. 11 is a view of the exterior side view of the Flexor catheter.

FIG. 11 shows a side view of the flexor depicting the recess 250 in the handle to reduce the profile of the control knob 216.

The construction details of the invention as shown in the preceding figures are that the useable length of the distal tubular section shall be sufficient to reach from a patient's vascular insertion site, in the groin area, to the left atrium of their heart, typically 50 to 75 centimeters, but may be longer in taller patients. As is well known only the proximal and distal section of the catheters illustrated to facilitate disclosure of the invention and the inventive features in the most proximal and distal areas of the catheters. The inner diameter of the distal tubular section shall be sufficient to accommodate various catheter devices, typically 5 French (1.65 mm) to 12 French (3.96 mm). The distal tubular section shall be made of a medical grade polymer and may include wire braiding within its wall. The distal tubular section 210 shall have coatings or a biomimetic surface on its patient-contacting surfaces to provide lubricity and/or deter the formation of blood clots. The side port tube shall be made of a medical grade polymer and have an external length of approximately 5 to 20-centimeters. The mechanical deflection actuator may be configured as a rotatable wheel, rotatable coaxial collar, slide, or lever. The figures depict the control knob actuator 214 as a rotatable wheel, other actuation mechanism may be employed.

Guider Device

Figure 12:
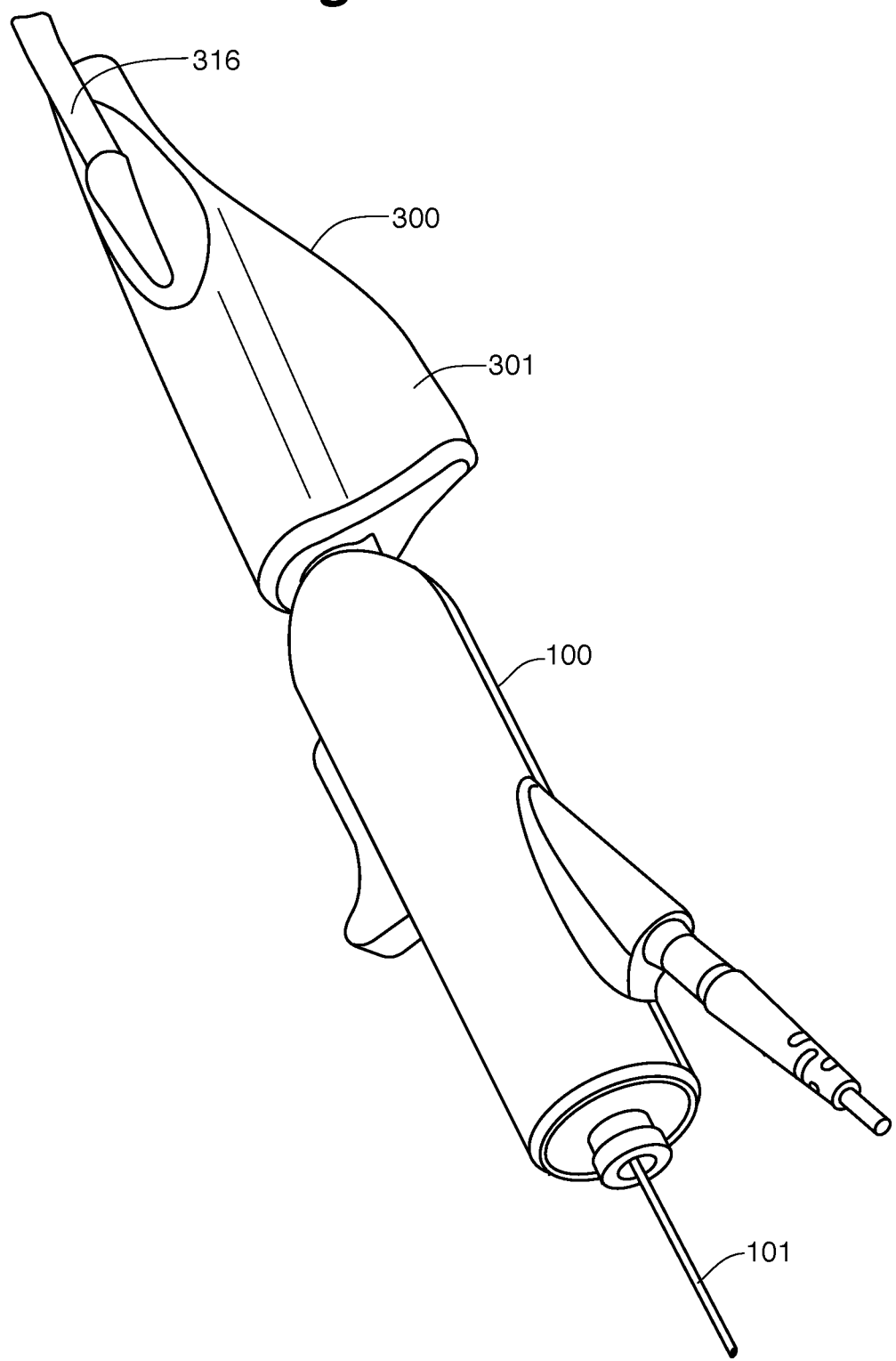
FIG. 12 is a perspective view of the Lancer coupled to the Guider.
Figure 13:
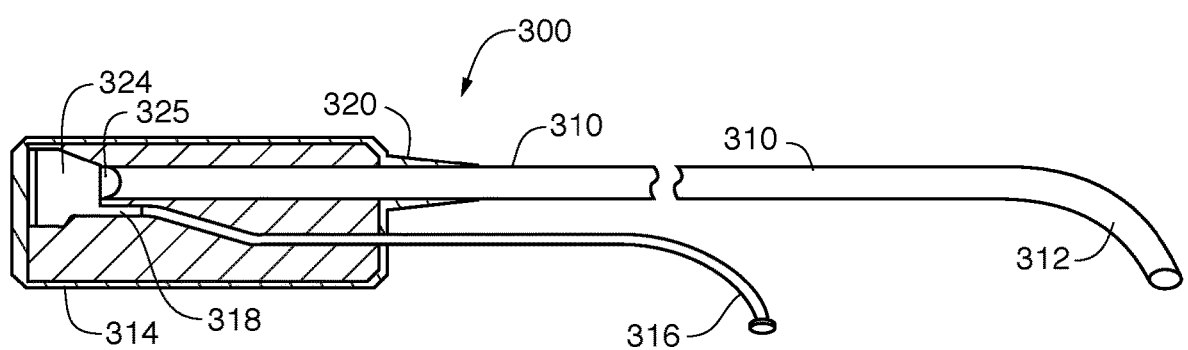
FIG. 13 is a cross section of the Guider.

FIG. 12 shows Guider 300 coupled to Lancer 100. FIG. 13 shows that Guider 300 provides a faired shaped section providing a torque handle 301 which forms a directional indication. The side port 310 does not cross the torque handle 301 and therefore does not interfere with the use of the torque handle 301. This arrangement eliminates interference and entanglement with adjacent devices, and mitigates the risks of clot formation on the blood-contacting surfaces of the introducer. Also seen in this figure is the most proximal section of a guide wire 101.

Referring now to the invention in more detail, in FIG. 13 there is shown the entire guiding vascular introducer device 300 comprised of a distal tubular section 310 that traverses through a proximal handle 314.

In further detail, still referring to the invention of FIG. 13, distal tubular section 310 has a curved tip section 312. The handle 314 is further comprised of a side port tube 316. The external part of the side port tube 316 is located at the distal end of the handle 312.

In the FIG. 13 there is shown a strain relief 320 at the junction of the distal tubular section 310 and handle 314 as well as a canted pass-through aperture 318 for the side port tube 316 to enter the handle 314.

The construction details of the invention are selected such that the useable length of the distal tubular section 310; including its curved tip section 312, shall be sufficient to reach from a patient's vascular insertion site, in the groin area, to the left atrium of their heart, typically 50 to 75 centimeters, but may be longer in taller patients. The inner diameter of the distal tubular section 310, including its curved tip section 312, shall be sufficient to accommodate various catheter devices, typically 5 French (1.65 mm) to 12 French 3.96 mm). The distal tubular section 310, including its curved tip section 312, shall be made of a medical grade polymer and may include wire braiding within its wall. The distal tubular section 310, including its curved tip section 312, shall have coatings on its patient-contacting surfaces to provide lubricity and/or deter the formation of blood clots. The side port tube 316 shall be made of a medical graced polymer and have an external length of approximately 5 to 20 centimeters. The handle 314 shall be a length sufficient to efficiently manipulate the introducer with the thumb and 3-5 fingers, typically between 3-5 centimeters. Furthermore, the handle 314 shall be of shape that provides an intuitive directional indicator that is in plane with the curved tip section 312. One such shape is an inverted teardrop, as depicted in FIG. 12. The handle 314, including the canted pass-through aperture 318, shall be made of a medical grade thermoplastic such as polycarbonate, polyethylene, or nylon.

Referring now to FIG. 13 there is shown the handle 314, distal tubular section 310, side port tube 316, strain relief 320, and canted pass-through aperture 318, Of note, the side port tube 316 and distal tubular section 310 exit from the handle 314 in a parallel orientation.

The construction details of the side port tube 116, distal tubular section 110, hemostasis valve housing 124 and mounting stem 118 shown in FIG. 13 are now described. The hemostasis valve housing 324 and integral mounting stem 325 are made of a medical grade thermoplastic such as polycarbonate, polyethylene, or nylon. The distal tubular section 310 is connected to the hemostasis valve housing 324 via injection molding or medical grade adhesive. The entire valve housing 324 shall be contained internally within the handle 314. The side port tube 316 is connected to the mounting stem 318 via medical grade adhesive.

The advantages of the present invention include, without limitation, is that it allows the operator to efficiently torque the introducer during a procedure. Typically, the operator only has a small hemostasis valve housing to serve as a torque handle. Furthermore, by removing the side port tube from the primary area of device manipulation eliminates the risks of interfering with operation and entangling with, and possibly dislodging, an adjacent device. Finally, the addition of a biomimetic coating on the patient-contacting surfaces with mitigate the risks of thrombogenesis, or the production of blood clots, which may lead to such adverse effects as stroke, myocardial infarction, or pulmonary embolus, all of which may be fatal.

In broad embodiment, the present invention is a guiding vascular introducer designed with an ergonomic torque handle with features that promote efficient and an improved safety profile.

Method of Use

The stepwise sequence of use proceeds as follows:
1. The physician uses the Seldinger procedure to gain access to the femoral vein with a conventional needle puncture.
2. A long guidewire is inserted through the needle and advanced under fluoroscopic guidance to the SVC.
3. Withdraw the needle over the wire leaving the wire in place.
4. The Lancer-Flexor or Lancer-Guilder is advanced into the wound and over the wire to the SVC.
5. Pull the GW into the Lancer.
6. Rotate the Lancer-Flexor or Lancer-Guider to point medial as to be perpendicular to the plane of the interarterial septum.
7. Connect the extension lead form Lancer to an EMG recording system to display unipolar signal from the distal tip of Lancer
8. While maintaining system alignment via monitoring fluoroscopic imaging, electro gram and optional ultrasound imaging to locate the fossa ovalis.
9. Once the fossa ovalis location has been confirmed hold the system securely and actuate the thumb lever to advance the puncture element through the fossa ovalis,
10. Optionally confirm presence in the left atrium via contrast injection of pressure recording, and advance the GW into the left atrium.
11. Release the thumb lever automatically retracting the puncture element under the force supplied by spring.
12. Advance system into the left atrium while monitoring the electro gram.
13. Holding the system securely release and uncouple Lancer and push sheath toward tip of Lancer.
14. With the Sheath near the wall of the atrium The Lancer is withdrawn from the sheath, and the sheath is aspirated and flushed with heparinized saline. The sheath is now placed for the desired intervention such as ablation or device placement.

Figure 14:
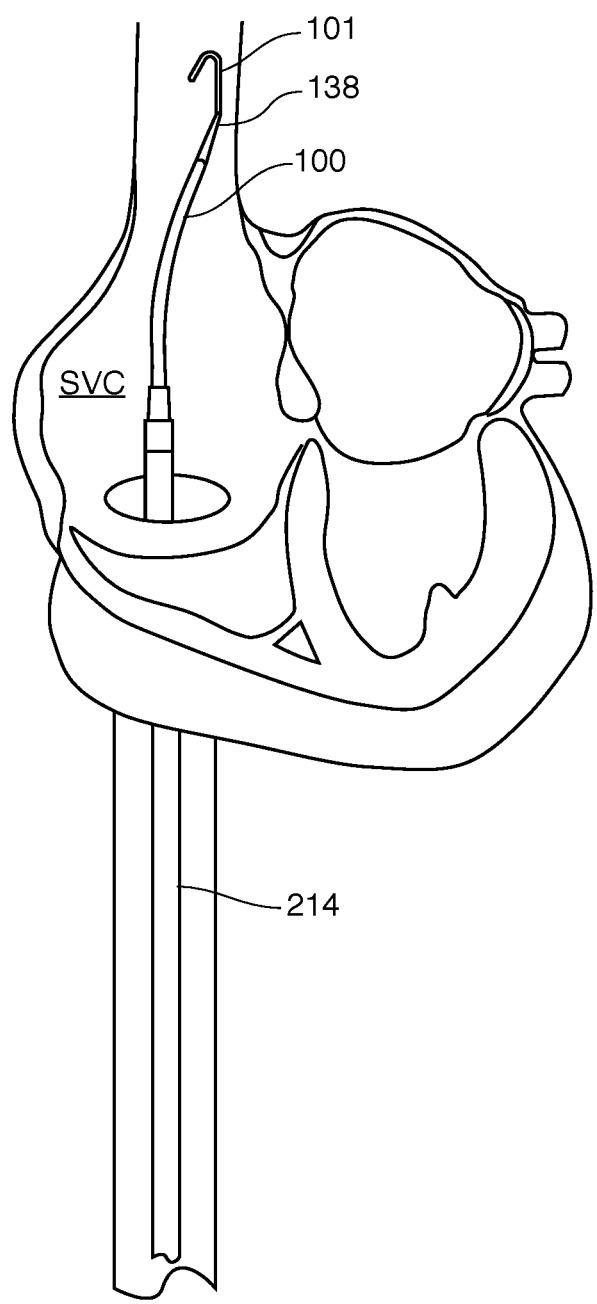
FIG. 14 shows the context of a step in the method.

FIG. 14 shows a state during the method. In the figure the Lancer 100 extends beyond the distal tip of the guiding sheath 214 in this instance of a Flexor device. The Flexor outer sheath 214 and Lancer 100 and the guidewire 101 move together to correspond to Steps 1 and 2 of FIG. 23.

Figure 15:
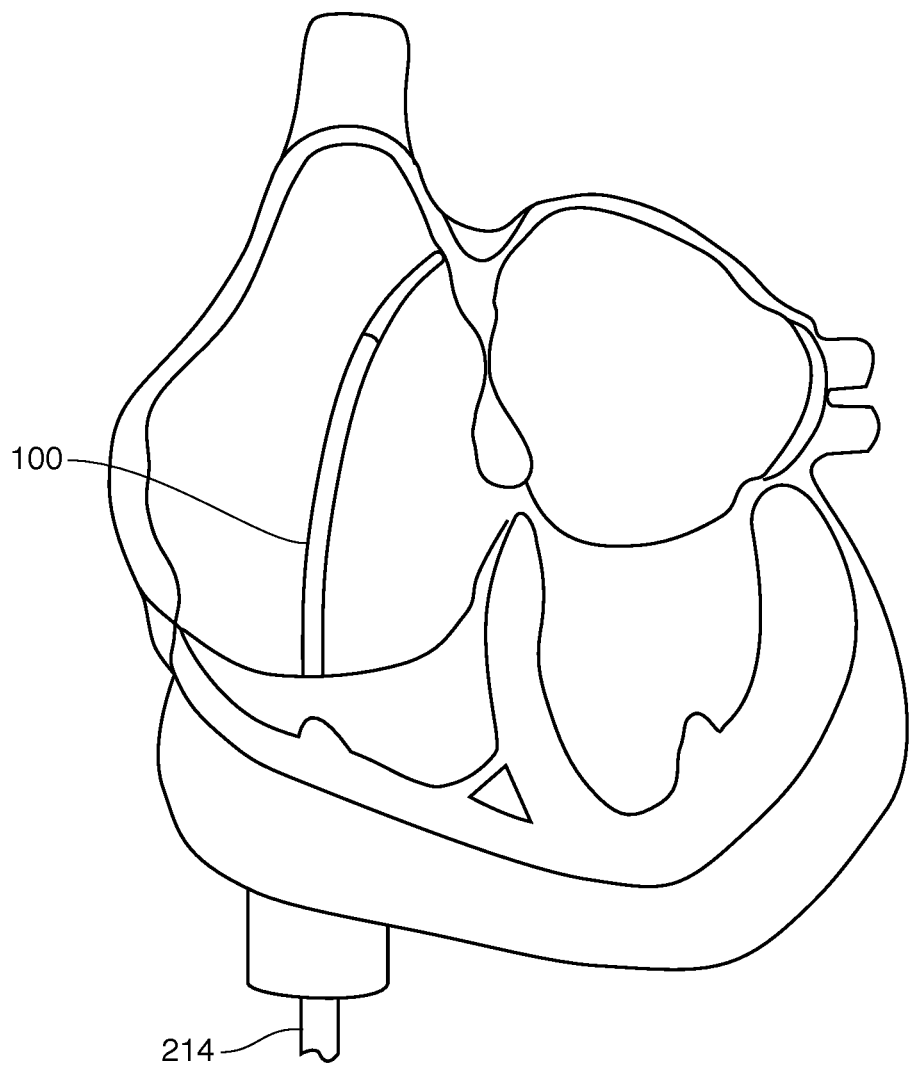
FIG. 15 shows the context of a step in the method.
Figure 16:
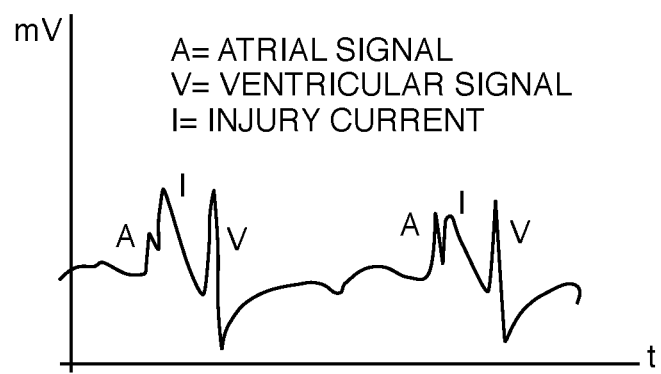
FIG. 16 shows the context of a step in the method.

FIG. 15 shows a state in the method. In the figure the GW is retracted into the Lancer 100. The system, Lancer 100 and flexor 200 are moved together and the distal tip of Lancer is dragged along the SVC to the high septal surface while recording and displaying the electrogram. A typical electrogram in this position is seen in FIG. 16, where the injury current is a response to the contact with the Lancer electrode. This corresponds to steps 5, 6 and 7 of FIG. 23.

Figure 17:
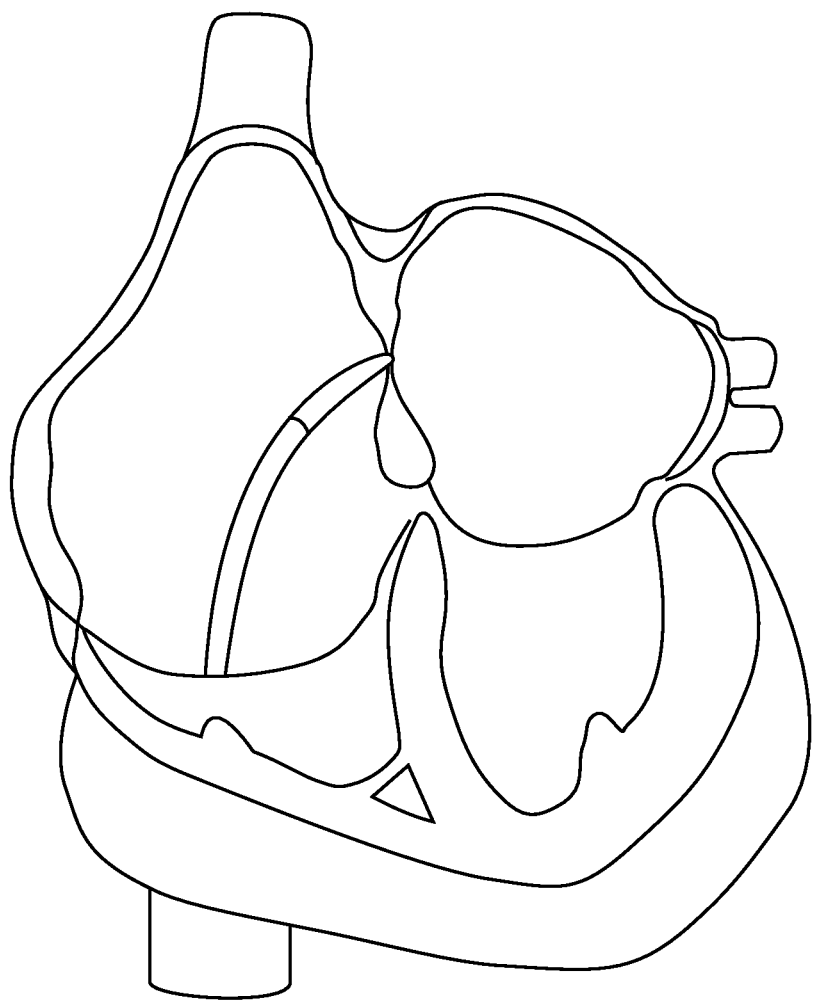
FIG. 17 shows the context of a step in the method.
Figure 18:
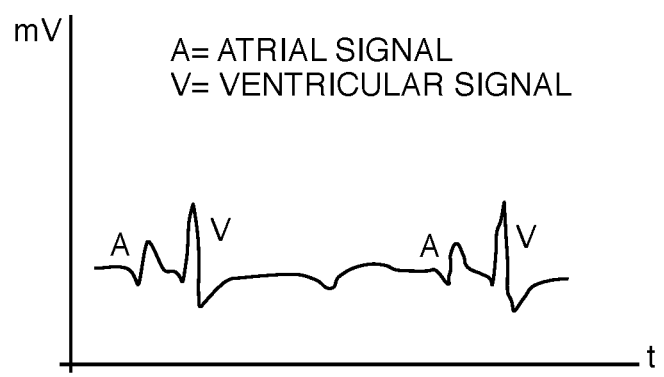
FIG. 18 shows the context of a step in the method.

FIG. 17 shows continued motion of the catheter pair an electrographic at FIG. 18, and visual confirmation of the Lancer 100 at the fossa ovalis.

Figure 19:
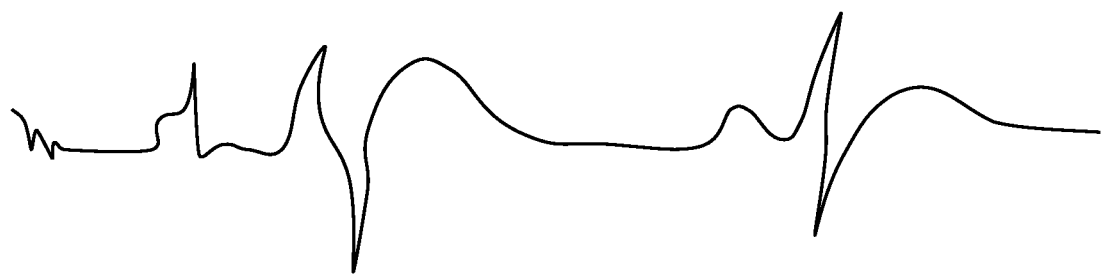
FIG. 19 shows the context of a step in the method.

FIG. 19 represents real time recording associated with the path depicted in FIG. 17. It is typical l for the time scale of the EMG recorder to preserve several seconds of EMG so that comparisons can be made over time by the physician.

Figure 22:
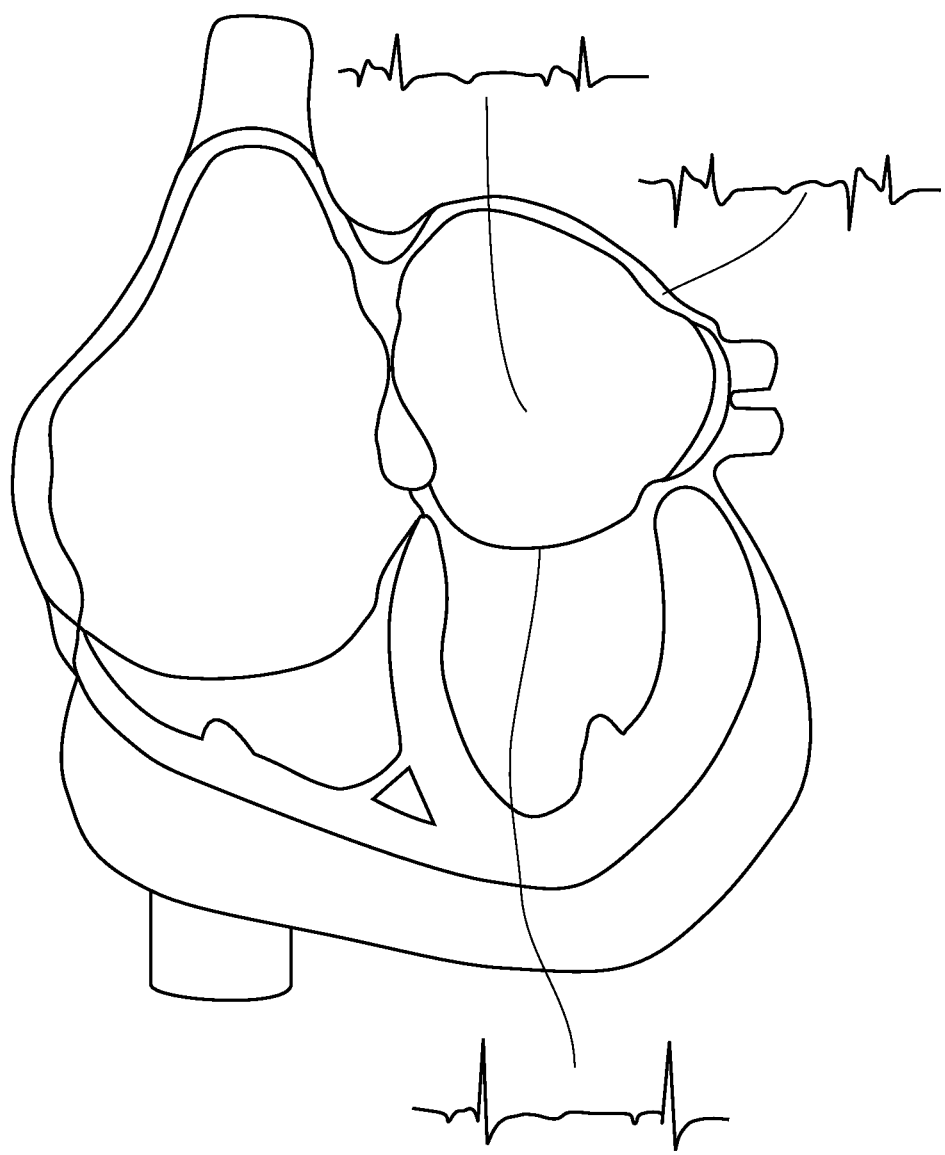
FIG. 22 shows the context of a step in the method.

FIG. 22 shows the characteristic electro grams that will be sensed by Lancer-Flexor or Lancer-Guider as it navigates the left heart atrium.

Figure 20:
FIG. 20 shows the context of a step in the method.
Figure 21:
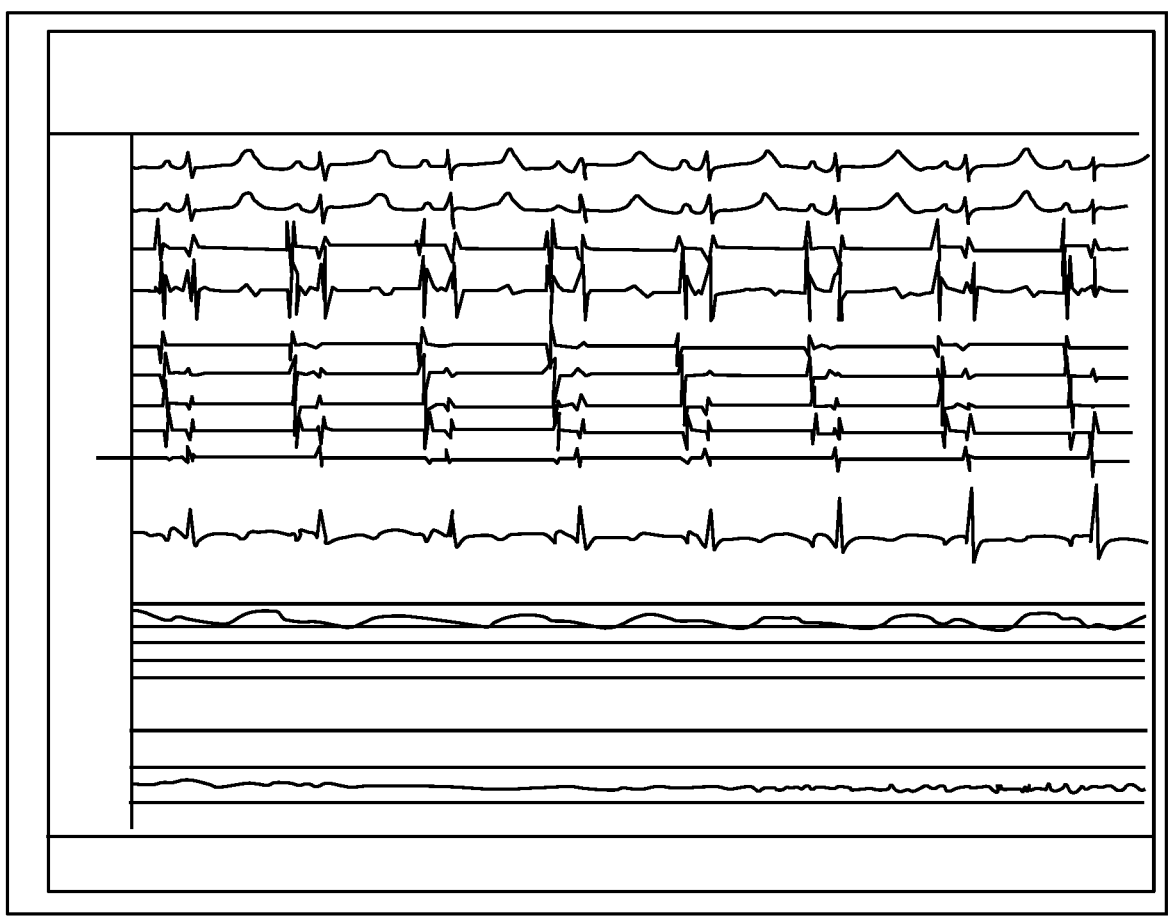
FIG. 21 shows the context of a step in the method.

FIG. 20 and FIG. 21 show the time domain representation of exploratory motions in side of the Left Atrium.

What is claimed:

1. A catheter system for crossing into the left heart from the right heart comprising:

an inner catheter, the inner catheter defining a needle lumen which extends from an inner catheter proximal end to an inner catheter distal end, a piercing needle positioned within the needle lumen, the piercing needle defining a guide wire lumen for receipt of a guidewire therethrough, the piercing needle having a piercing needle distal tip, the inner catheter proximal end further comprising an inner catheter handle having a thumb lever, the thumb lever being actuatable between an unactuated state and an actuated state, in the unactuated state the piercing needle distal tip does not extend distally out of the needle lumen, and in the actuated state the piercing needle distal tip extends distally out of the needle lumen, the inner catheter handle further comprising an electrical connector in electrical contact with the piercing needle;

the guide wire, the guide wire having a guide wire distal tip; and an outer catheter which defines an outer catheter lumen which extends from an outer catheter proximal end to and outer catheter distal end, the outer catheter lumen sized to accept the inner catheter therethrough, the outer catheter distal end is deflectable along an arc of a plane, a control knob is positioned at the outer catheter proximal end, the control knob configured to turn on a control axis, the control knob is in communication with a pinion, the pinion is in communication with a first rack and a second rack, a first pull wire anchored to and extending between the first rack and the outer catheter distal end, a second pull wire anchored to and extending between the second rack and the outer catheter distal end, whereby turning the control knob in a first direction about the control axis causes the pinion to move the first rack and the first pull wire in a first longitudinal direction and the second rack and the second pull wire in a second longitudinal direction opposite to that of the first longitudinal direction, resulting in the outer catheter distal end being deflected through an arc of up to 180 degrees.

2. The system of claim 1 further comprising a spring, the spring located within said inner catheter handle, the spring biasing the thumb lever into the unactuated state.

3. The system of claim 1, wherein the control knob includes a thumb actuated control button, the control button having an actuated position and an unactuated position, in the actuated position the control knob is free to turn about the control knob axis, in the unactuated position the control knob is locked into its current position.

4. The system of claim 1, wherein the control knob positioned at the outer catheter proximal is configured for left handed use.

5. The catheter system of claim 1 further comprising a display, the display in electronic communication with the electrical connector and the piercing needle, the catheter system displaying at the display an electrogram formed by contacting the distal end of the inner catheter along with an electrode to a first anatomical region of the heart while the thumb lever is in the unactuated state and the piercing needle distal tip does not extend distally out of the needle lumen.

6. The catheter system of claim 5 wherein the electrogram includes an injury current.

7. A catheter system for crossing into the left heart from the right heart comprising:

an inner catheter, the inner catheter defining a needle lumen which extends from an inner catheter proximal end to an inner catheter distal end, a piercing needle positioned within the needle lumen, the piercing needle defining a guide wire lumen for receipt of a guidewire therethrough, the piercing needle having a piercing needle distal tip, the inner catheter proximal end further comprising an inner catheter handle having a thumb lever, the thumb lever being actuatable between an unactuated state and an actuated state, in the unactuated state the piercing needle distal tip does not extend distally out of the needle lumen, and in the actuated state the piercing needle distal tip extends distally out of the needle lumen, the inner catheter handle further comprising an electrical connector in electrical contact with the piercing needle;

the guide wire, the guide wire having a guide wire distal tip; and an outer catheter which defines an outer catheter lumen which extends from an outer catheter proximal end to and outer catheter distal end, the outer catheter lumen sized to accept the inner catheter therethrough, the outer catheter proximal end defining a torque handle and a side port in communication with the outer catheter lumen, wherein the side port does not cross the torque handle.

8. The system of claim 7 further comprising a spring, the spring located within said inner catheter handle, the spring biasing the thumb lever into the unactuated state.

9. The catheter system of claim 7 further comprising a display, the display in electronic communication with the electrical connector and the piercing needle, the catheter system displaying at the display an electrogram formed by contacting the distal end of the inner catheter along with an electrode to a first anatomical region of the heart while the thumb lever is in the unactuated state and the piercing needle distal tip does not extend distally out of the needle lumen.

10. The catheter system of claim 9 wherein the electrogram includes an injury current.

11. The catheter system of claim 7 wherein the torque handle has a longitudinal axis as defined by the outer catheter lumen, the side port being aligned with the longitudinal axis.

* * * * *